United States Patent [19]

Khanna et al.

[11] Patent Number: 4,544,765

[45] Date of Patent: Oct. 1, 1985

[54] CHLORAMPHENICOL DERIVATIVES

[75] Inventors: Pyare Khanna, San Jose; Evan S. Snyder, Mountain View; Prithipal Singh, Sunnyvale, all of Calif.

[73] Assignee: Syra Company, Palo Alto, Calif.

[21] Appl. No.: 676,689

[22] Filed: Nov. 30, 1984

Related U.S. Application Data

[62] Division of Ser. No. 256,761, Apr. 23, 1981, Pat. No. 4,489,156.

[51] Int. Cl.$^4$ ............... C07C 87/64; C07C 101/44
[52] U.S. Cl. ................... 560/29; 562/426; 562/433; 564/212; 564/213; 568/423; 568/424
[58] Field of Search .............. 260/112 R, 112 B; 564/212, 213; 560/43, 29; 435/7, 177; 562/433, 426; 568/423, 424

[56] References Cited

U.S. PATENT DOCUMENTS

| | | | |
|---|---|---|---|
| 2,483,884 | 10/1949 | Crooks, Jr. et al. | 564/213 |
| 2,483,885 | 10/1949 | Crooks, Jr. et al. | 564/213 |
| 2,538,764 | 1/1951 | Crooks, Jr. et al. | 564/212 |
| 2,686,788 | 8/1954 | Moore et al. | 564/213 |
| 3,592,949 | 7/1971 | Teach et al. | 560/29 |
| 4,214,001 | 7/1980 | Engelhardt et al. | 560/29 |

*Primary Examiner*—John Kight
*Assistant Examiner*—Nathan M. Nutter
*Attorney, Agent, or Firm*—Theodore J. Leitereg; Bertram I. Rowland

[57] ABSTRACT

Chloramphenicol derivatives are provided for use in the preparing of antigen conjugates for the production of antibodies specifically for chloramphenicol. Specifically, the aryl amino group is derivatized to introduce a non-oxocarbonyl group which is used for amide formation with an antigen. The conjugate is then injected into a vertebrate for production of antisera which is isolated in conventional ways and find particular use in competitive protein binding assays.

5 Claims, No Drawings

CHLORAMPHENICOL DERIVATIVES

This is a division of copending application U.S. Ser. No. 256,761, filed Apr. 23, 1981, now U.S. Pat. No. 4,489,156.

BACKGROUND OF THE INVENTION

In performing immunoassays, it is necessary to have a receptor which specifically recognizes the compound or compounds of interest while having weak or no binding to compounds of similar structure which may be encountered in the samples of interest. In order to obtain antisera, when haptens are involved, it is necessary that derivatives of the hapten be designed for conjugation to an antigen, where the resulting antisera will provide for the desired specificity. In many situations, the hapten of interest is highly functionalized, so that the synethetic procedure for the derivative must be designed to maintain the integrity of the structural features of the haptens.

DESCRIPTION OF THE PRIOR ART

U.S. Pat. No. 3,817,837 describes an enzyme immunoassay. Hamburger and Douglass, Immunology 1969, 17(4), 599–602; Orgel and Hamburger, ibid, 1971, 20(2), 233–9; Hamburger and Douglass, ibid, 1969, 17(4), 58791 and Hamburger, Science 152 (379), 203–5 (1966) describe various antibodies to chloramphenicol.

SUMMARY OF THE INVENTION

Chloramphenicol derivatives are prepared for conjugation to poly(amino acids) to prepare antigens for the production of antibodies and enzyme conjugates, where the enzyme conjugates and antibodies are used in combination for the determination of chloramphenicol. Particularly, the nitro group of chloramphenicol is reduced and the resulting aromatic amino group functionalized to provide a carbonyl functionality to react with the amino groups of the poly(amino acids) to provide a linking group. The conjugated antigens are employed in conventional ways for the production of antibodies specific for chloramphenicol.

DESCRIPTION OF THE SPECIFIC EMBODIMENTS

The subject invention is concerned with the preparation of reagents for use in diagnostic immunoassays for chloramphenicol. Specifically, the nitro group of chloramphenicol is reduced to an amino group and the resulting amino group functionalized to provide for an oxo-carbonyl functionality for linking to available amino groups of the poly(amino acid). The carbonyl functionality will normally be separated from the ar-amino group by a chain of at least about 2 atoms and not more than about 8 atoms, preferably 3 to 5 atoms. The atoms may be carbon, nitrogen, chalcogen (oxygen and sulfur), usually carbon and oxygen, there normally being from 0 to 1 heteroatom in the chain, where the heteroatoms are bonded solely to carbon atoms, with chalcogen normally bonded to saturated carbon. With oxo-carbonyl, a single bond will usually be formed by reductive amination with available amino groups of the poly(amino acid), while with carboxy groups, peptide bonds will normally be formed. The carboxy derivative can be activated in a variety of ways to form peptide bonds.

For the preparation of antibodies, the chloramphenicol derivative will be conjugated to an antigenic poly(amino acid), which may then be injected into vertebrates, particularly domesti animals, for production of antibodies. After a repeated number of injections based on a predetermined schedule, the antibodies may be harvested from the serum and may be used as obtained or further purified so as to concentrate the antibodies of interest.

For the most part, the compositions of this invention will have the following formula:

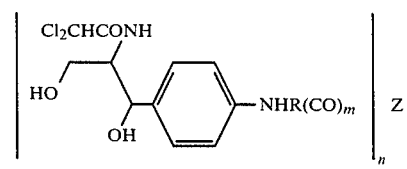

wherein:

R is an aliphatic linking group of from 2 to 12 atoms other than hydrogen, normally having from about 2 to 8 atoms in the chain, preferably 2 to 6, more preferably 3 to 5, wherein the atoms in the chain are carbon, nitrogen, and chalcogen of atomic number 8 to 16 (oxygen and sulfur), wherein the heteroatoms are bonded to other than hydrogen and chalcogen is bonded solely to saturated carbon; of particular interest are 1-oxopolymethylenes with the oxo bonded to the nitrogen.

Z is hydrogen, hydroxyl, alkoxy of from about 1 to 6 carbon atoms, more usually of 1 to 3 carbon atoms, an activating group capable of activating the non-oxo-carbonyl for forming peptide bonds in an aqueous medium with a poly(amino acid) e.g. p-nitrophenyl ester or N-oxy succinimide ester or Y, wherein Y is a poly(amino acid) residue, either a polypeptide or protein having 1 or more subunits, of at least about 5000, more usually at least about 10,000 molecular weight and may be 10,000,000 or more molecular weight, usually not more than 1,000,000, functioning as either an antigen or enzyme;

m is 0 or 1, being 1 when Z is other than Y; and n is at least 1, being 1 when Z is other than Y and when Y being 1 to the molecular weight of Y divided by 2000, more usually divided by 3000, generally being from about 10 to 100 when Y acts as an antigen and is of molecular weight of from about 30,000 to 300,000 and of from about 2 to 20, more usually 2 to 16, when Y functions as an enzyme.

Preferred R groups include alkylene, alkenylene, alkyleneoxyalkylene (wherein heteroatoms are separated by at least 2 carbon atoms), N-lower alkyl (1–3 carbon atoms) alkyleneaminoalkylene (wherein the heteroatoms are separated by at least 2 carbon atoms).

The compounds of primary interest are those where Z is Y and find use as antigens or enzymes, Y being a poly(amino acid), either antigenic or an enzyme. These compounds will for the most part have the following formula:

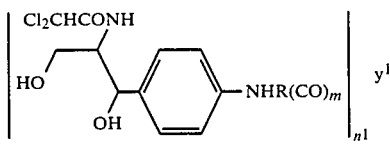

wherein R and m have been defined previously;

$Y^1$ is a poly(amino acid), functioning as an antigen or enzyme, of at least about 2000 molecular weight, more usually of at least about 10,000 molecular weight and may be up to 10,000,000 molecular weight or greater, generally not exceeding about 600,000 molecular weight, more usually not exceeding about 300,000 molecular weight;

$n^1$ is at least 1, usually greater than 1, and generally not exceeding the molecular weight of $Y^1$ divided by 1000, more usually divided by 2000 and will usually be at least the molecular weight of $Y^1$ divided by 100,000, more usually the molecular weight of $Y^1$ divided 50,000, generally being from about 1 to 100, more usually from about 5 to 80, when $Y^1$ is functioning as an antigen, and from about 1 to 30, more usually 2 to 16, when $Y^1$ is functioning as an enzyme.

With intermediate molecular weight antigens, those having molecular weights in the range of about 20,000 to 600,000 the number of chloramphenicol groups which are bonded to the antigen will generally be from about 5 to 100, more usually from about 20 to 90, while with low molecular weight antigens, those from about 2000 to 10,000 molecular weight, the number will generally be from about 1 to 20, more usually 2 to 10.

As indicated previously, of particular interest are compounds where the oxo-carbonyl group (other than keto) and the non-oxo-carbonyl group are bonded to an amino group, which is part of a polypeptide or protein structure. One group of polypeptides and proteins is antigenic, so that by bonding the carbonyl derivative of chloramphenicol to the polypeptide or protein, antibodies can be formed to chloramphenicol. A narrower class of proteins, which also can be used as antigens, but will not normally be used as such, are enzymes which are employed as the detector in an immunoassay system. As antigens, inactive enzymes can be used.

Polypeptides (referred to generally in the invention as poly(amino acid)) usually encompass from about 2 to 100 amino acid units (usually less than about 12,000 molecular weight). Larger polypeptides are arbitrarily called proteins. Proteins are usually composed of from 1 to 20 polypeptide chains called subunits, which are associated by covalent or noncovalent bonds. Subunits are normally of from about 100 to 300 or higher amino acid groups (or 10,000 to 35,000 or higher molecular weight). For the purposes of this invention, poly(amino acid) is intended to include individual polypeptide units and polypeptides which are subunits of proteins, whether composed solely of polypeptide units or polypeptide units in combination with other functional groups, such as porphyrins, as in haemoglobin or cytochrome oxidase.

The number of chloramphenicol groups will vary depending upon whether the poly(amino acid) is an enzyme or antigen. The maximum number of groups will be limited by the effect of substitution on solubility, activity, and the like. For the formation of antibodies, a sufficient number of chloramphenicol groups should be present, so as to provide a satisfactory harvest of antibodies to chloramphenicol. Otherwise, the proportion of antibodies to chloramphenicol as compared to antibodies to other compounds may be undesirably low. With monoclonal antibodies a reasonable number of hybridomas should result which secrete useful antibodies.

The first group of protein materials or polypeptides which will be considered are the antigenic polypeptides. These may be joined to the carbonyl group of the chloramphenicol analog through an amino group. The product can be used for the formation of antibodies to chloramphenicol. The protein materials which may be used will vary widely, and will normally be from 1000 to 10 million molecular weight, more usually 20,000 to 600,000 molecular weight.

Enzymes will normally be of molecular weights in the range of about 10,000 to 600,000, usually in the range of about 12,000 to 150,000, and more usually in the range of 12,000 to 80,000. Some enzymes will have a plurality of enzyme subunits. It is intended when speaking of enzyme molecular weights to refer to the entire enzyme. There will be on the average at least about 1 chloramphenicol per enzyme, when the labeling is not limited to a specific amino group, and rarely more than 30 chloramphenicols per enzyme, usually not more than 20 chloramphenicols per enzyme. For example, with lysozyme the average number of chloramphenicol groups would be in the range of about 2 to 5. For glucose-6-phophate dehydrogenase the average number will be in the range of 2 to 20.

While the chloramphenicol analog may be bonded through the non-oxo-carbonyl group to hydroxyl or mercapto groups, which are present in the poly(amino acids), for the most part the bonding will be to amino. Therefore, the compounds are described as amides, although esters and thioesters may also be present. The aldehyde derivative will be bonded solely to amino to form alkylamine groups through reductive amination.

Amino acids present in proteins which have free amino groups for bonding to the carbonyl-modified-chloramphenicol include lysine, N-terminal amino acids, etc. The hydroxyl and mercaptan containing amino acids include serine, cysteine, tyrosine and threonine.

Various protein and polypeptide types may be employed as the antigenic material. These types include albumins, serum proteins, e.g. globulins, ocular lens proteins, lipoproteins, etc. Illustrative proteins include bovine serum albumin, keyhole limpet hemocyanin, egg albumin, bovine gamma-globulin, etc. Small neutral polypeptides which are immunogenic such as gramicidins may also be employed. Various synthetic polypeptides may be employed, such as polymers of lysine, glutamic acid, phenylalanine, tyrosine, etc., either by themselves or in combination. Of particular interest is polylysine or a combination of lysine and glutamic acid. Any synthetic polypeptide must contain a sufficient number of free amino groups as, for example, provided by lysine.

The second group of protein molecules are the detectors. These are the enzymes to which the carbonyl modified chloramphenicol may be conjugated. As indicated, the chloramphenicol conjugated enzyme is useful for immunoassays. A description of the immunoassay technique will follow.

Various enzymes may be used such as peptidases, esterases, amidases, phosphorylases, carbohydrases, oxidases, e.g. dehydrogenase, reductases, and the like. Of particular interest are such enzymes as lysozyme, perosidase, α-amylase, β-galactosidase, dehydrogenases, particularly malate dehydrogenase and glucose-6phosphate dehydrogenase, alkaline phosphatase, βglucuronidase, cellulase and phospholipase. In accordance with the I.U.B. Classification, the enzymes of interest are: 1. Oxidoreductases, particularly Groups 1,1, and more particularly 1.1.1, and 1.11, more particularly, 1.11.1; and 3. Hydrolases, particularly 3.2, and more particularly 3.2.1.

The substituted enzymes will for the most part have the following formula:

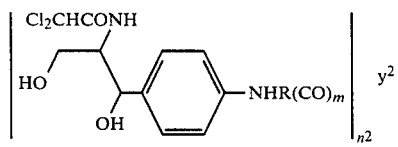

wherein:

m and R have been defined previously;

$Y^2$ is an enzyme substituted at other than the active site, and having at least 30, preferably at least 50 percent of its original activity prior to conjugation; and $n^2$ will usually be of from 1 to 30, more usually from 2 to 20, preferably 2 to 14, more preferably 2 to 12, but generally on the average not more than about 60 percent of the total lysine groups available in the enzyme, although small enzymes such as lysozyme may have all available lysine groups conjugated.

In forming the various amide products which find use in the subject invention, the carboxylic acid will normally be activated. This can be achieved in a number of ways. Two ways of particular interest are the reaction with a carbodiimide, usually a water soluble dialiphatic or dicycloaliphatic carbodiimide in an inert polar solvent, e.g. dimethylformamide, acetonitrile or hexamethylphosphamide. The reaction is carried out by bringing the various reagents together under mild conditions and allowing sufficient time for the reaction to occur.

Another way is to use esters of the carboxy modified chloramphenicol which are operative in water for acylating amine functions. Illustrative of groups bonded to carboxy to provide activated esters which can be used in water are p-nitrophenyl and N-succinimidyl. For the aldehyde conjugation, a reductive amination is carried out in a polar, usually aqueous medium, employing sodium cyanoborohydride as the reducing agent.

The antibodies which are prepared in response to the conjugated antigens of this invention have strong specific binding to the parent drug, the conjugated antigen, the compound or derivative thereof used to conjugate to the antigen, and the chloramphenicol labeled compounds, e.g. enzyme conjugates.

As previously indicated, the subject enzyme conjugates and antibodies find use in immunoassays. The enzyme conjugates of the subject invention are particularly useful in the method described in U.S. Pat. No. 3,817,837. In performing an effective immunoassay, there are many considerations. Since the aforementioned assay is spectrophotometric, one desires that there be a substantial change in signal with changing concentration of the analyte in the range of interest of the analyte. Thus, the antigenic conjugate must provide antibodies which when employed in combination with the enzyme conjugate, results in a sensitive response to variations in the chloramphenicol concentration.

In addition, there are a number of considerations about the antigen. Normally, one immunizes a number of animals with the antigen. Initial bleeds tend to have low titer of low binding affinity, but within a relatively short time a plateau of titer and affinity is reached. A good antigen provides a high titer and a high average affinity with most or all the animals immunized. One of the significant advantages of a high affinity high titer is that one can use smaller amounts of the antisera in that the antibody of interest is a larger proportion of the total amount of gamma-globulin.

There is the further consideration of cross-reactivity. When determining a drug, one does not wish other drugs or naturally occurring compounds to affect the observed signal. Where other compounds are able to bind to various degrees to the antisera, the other compounds can have a substantial affect on the signal. This can be particularly true with metabolites, which are not in themselves active in the same manner as the drug precursor. Thus, in many situations, the antigen precursor must be designed to provide antibodies which will not significantly bind to metabolites of the analyte of interest.

EXPERIMENTAL

The following examples are offered by way of illustration and not by way of limitation.

All temperatures not otherwise indicated are centigrade. Percents and parts not otherwise indicated are by weight, except for mixtures of liquids which are by volume. Abbreviations which are employed are as follows: THF—tetrahydrofuran; tlc—thin layer chromatography; h—hour; DCC—dicyclohexyl carbodiimide; NHS—N-hydroxy succinimide; HOAc—acetic acid; BSA—bovine serum albumin; EDAC—ethyl dimethylaminopropyl carbodiimide.

EXAMPLE I

Preparation of the 1-p-adipamidophenyl-2-dichloroacetamido-1,3-propanediol conjugate of bovine serum albumin A. A solution of oxalyl chloride (7.94 g, 62.5 mmol) and adipic acid monomethylester (4.0 g, 25 mmol) in benzene (20 ml) was heated to reflux under argon for 30 min, then allowed to stir over night under argon for 16 h. The reaction mixture was distilled at slightly reduced pressure to remove benzene and oxalyl chloride, then at 73° C. and 0.2 mm to afford 4.46 g (100%) of a colorless oil.

B. To a solution of N-1,3-dihydroxy--(p-anilino)propyl dichloroacetamide (703 mg, 2.39 mmol) in THF (17 ml) and Et₃N (0.5 ml) at 0° under argon was added adipic acid chloride monomethylester (853 mg, 4.78 mmol) in THF (3 ml) dropwise over 30 min and the reaction was allowed to stir warming to room temperature over 90 min. Tlc indicated that two new products, bisacylated and monoacrylated had been formed in nearly equal amounts. The reaction mixture was poured into ice/HCl (pH=1), extracted with ethyl acetate (3×100 ml), washed (saturated brine), dried (Na₂SO₄) and concentrated. Nmr confirmed that the two spots on tlc were due to mono and bisacylated starting materrial. This reaction mixture was hydrolyzed without further purification.

C. To a solution of the above mixture (1.29 g, 2.23 mmol) in methanol (15 ml) at 0°–4° was added an aqueous 5% sodium carbonate solution (18 ml) dropwise over 1 h. Stirring at 4° was continued for 27 h. Tlc indicated incomplete hydrolysis, therefore 5% sodium carbonate (4.5 ml) was added dropwise and the reaction was allowed to stir at 4° for an additional 15.5 h. At this time an additional 4.5 ml of 5% sodium carbonate was added and stirring was continued for 4 h. The reaction mixture was poured into ice/HCl (20 ml), was made acidic (pH=1), extracted with ethyl acetate (4×100 ml), washed (brine), dried ($Na_2SO_4$) and concentrated to afford 1.05 grams of crude material. Preparative thin layer chromatography on silica gel plates eluting with methylene chloride (83%) and methanol (17%) afforded 160 mg (16%) of the mono-N-adipoyl product, and 309 mg of partially hydrolyzed material. The latter was redissolved in methanol (5 ml) at 4° and to it was added 5% sodium carbonate solution (5.5 ml). This reaction mixture was allowed to stir for 4 days, was quenched with ice/HCl (pH=1), extracted with ethyl acetate, dried ($Na_2SO_4$) and concentrated. Preparation tlc on silica eluting with methylene chloride/methanol/dichloroacetic acid (84/16/0.1, v/v/v) afforded 160 mg (16%) of the desired product.

D. To a solution of the above product (C) (160 mg, 0.38 mmol) in dry THF (20 ml) under argon at 0° was added DCC (165 mg, 0.8 mmol) and NHS (46 mg, 0.4 mmol) and the reaction mixture was allowed to stir for two days. Tlc ($CH_2Cl_2$/MeOH/HOAc, 85/15/0.1) indicated incomplete reaction and therefore DCC (83 mg, 0.4 mmol) and NHS (23 mg, 0.2 mmol) were added. Stirring at 0°–4° was continued for 24 h. at which time the reaction mixture was filtered, evaporated, washed with hexane, evaporated, dissolved in THF (10 ml) and added dropwise to a solution of BSA in phosphate buffer (20 ml) pH=8.5) at 0° and the reaction was allowed to stir for 30 h. Centrifugation at 10K. and 4° for 30 min. followed by dialysis against water (1×4L), followed by Sephadex G-25 (100 g, 500 ml) chromatography, then followed by dialysis against water afforded 449 mg (88%) of protein conjugate. The hapten number, determined by UV extinction coefficients was found to be between 21 and 25 ($\lambda_{max}$=246).

EXAMPLE II

Preparation of the 1-p-adipamidophenyl-2-dichloroacetamido-1,3-propanediol conjugate of glucose-6-phosphate dehydrogenase 1-p-(Adipamidophenyl)-2-dichloroacetamido-1,3-propanediol (0.0053 g), 0.0018 g of NHS and 0.0029 g of EDAC were weighed into a dry 2-necked flask. After further drying the flask and its content overnight, 250 μl of dimethylformamide was added into the flask and the solution formed was stirred for four hours at 25° C. Sixty-five μl of this solution was slowly added over a period of 5.25 hours to a 4° C. solution containing 0.6 mg of glucose-6-phosphate dehydrogenase (Beckman Co., Fullerton, Calif.) 30 mg glucose-6-phosphate disodium salt (Sigma Co.) and 20 mg of nicotinamide adenine dinucleotide reduced (Sigma Co.) in 0.5 ml of 0.055M Tris buffer, pH 8, and 0.2 ml of carbitol. The pH of the reaction mixture throughout the 5.25 hour period was maintained in the range of 8.5 to 9.5 using 0.1N sodium hydroxide. At the end of the reaction period, the reaction mixture was chromatographed on a 19×1.9 cm column of Sephadex G-50 (Pharmacia, Piscataway, N.J.) and eluted with 0.055M Tris buffer, pH 8, containing 0.05% sodium azide and 0.005% thimerosol. 1.4 ml fractions were collected and those fractions containing high enzyme activity (usually fractions 7 to 10) were pooled and were used as the adipamido-chloramphenicol glucose-6-phosphate dehydrogenase conjugate.

The compositions prepared above were used in an assay for chloramphenicol. The assay employed the following reagents:

TABLE I

| | |
|---|---|
| Buffer: | 0.055 M Tris-HCl, pH 8.1 (RT), 0.05% $NaN_3$, 0.005% Thimerosal |
| Assay Buffer: | Buffer, 0.5% NaCl, 0.01% (v/v) Triton X-100, pH 8.1 (RT) |
| Reagent A: | Buffer, 1.0% RSA, G6P($Na_2$), NAD, pH 5 (RT) antichloramphenicol optimized for response |
| Reagent B: | Buffer, 0.9% NaCl, 1.0% RSA, 0.032 M G6P(Na), pH 6.2, sufficient enzyme to give a maximum rate of 700 ΔOD. |

Protocol: 50 μl of the sample is drawn up into a diluter and dispensed with 250 μl of the assay buffer into a 1 ml Croan cup. A 50 μl aliquot of the diluted sample is drawn up and dispensed with a 250 μl portion of assay buffer into a second Croan cup. Into the second Croan cup is introduced 50 μl of the antibody reagent with 250 μl of the assay buffer, followed by the addition of 50 μl of the enzyme reagent and 250 μl of the assay buffer. Immediately after the enzyme addition, the entire sample is aspirated into the flow cell. After 15 sec. a first reading is taken, followed by a second reading after a 30 sec. interval. The results are reported as the difference in absorbance×2.667.

Four sheep were immunized with the antigen according to Example I. The antisera produced at the C bleed were tested for optimal assay response (O.D.) and for effective titer. The optimal assay response is the optimal separation in O.D. units between 2.5 μg/ml and 40 μg/ml chloramphenicol calibrators. This response shows the best range of the standard curve obtainable in accordance with the above described protocol. The larger the optimal assay response, the better the precision and accuracy. Effective titer is the amount of antiserum required per assay to give the optimal assay response. The higher the titer, the lower the required quantity of antiserum, the less expensive the assay production costs and the less extraneous material introduced into the assay medium. The following table reports the results of the four antisera.

TABLE II

| Antiserum | Optional Assay Response O.D. | Effective Titer (μl) |
|---|---|---|
| 3430C | 135 | 0.8 |
| 3431C | 133 | 0.8 |
| 3432C | 148 | 1.2 |
| 3433C | 134 | 2.0 |

Cross reactivity was determined against metabolites of chloramphenicol as well as other drugs. Of the three known metabolites of chloramphenicol, 1-p-nitrophenyl-2-amino-1,3-propanediol; 1-p-aminophenyl-2-dichloroacetamido-1,3-propanediol; and 1-p-aminophenyl-2-amino-1,3-propanediol, only the second metabolite showed significant activity, which is defined as the concentration of a compound which, when spiked into a 15 μg/ml control, will give a response in the assay equal to the response of 130% (i.e. 19.5 μg/ml) of the concentration of the 15 μg/ml) control, the cross reactivity concentration for the second compound was 2 μg/ml. Besides this metabolite, the chloramphenicol/succinate salt and thiamphenicol showed similar cross reactivity. Based on an independent study of a comparison between the above assay and HPLC with patient samples, which showed good correlation statistics between the two techniques, the effect of the cross reactivity on the subject assay to correctly quantitate chloramphenicol is believed to be minimal.

The compositions of the subject invention provide for reagents which provide a sensitive accurate assay for chloramphenicol, distinguishing chloramphenicol from closely related metabolites. The anitgenic conjugate provides for the efficient production of antibodies having high affinity and high titer for chloramphenicol. The combination of the antibodies and enzyme conjugates result in an accurate rapid assay for chloramphenicol in serum.

Although the foregoing invention has been described in some detail by way of illustration and example for purposes of clarity of understanding, it will be obvious that certain changes and modifications may be practiced within the scope of the appended claims.

What is claimed is:

1. A compound of the formula:

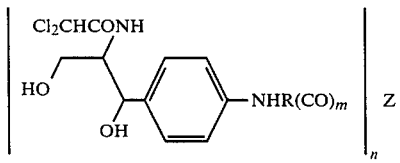

wherein:

R is an aliphatic linking group of up to 12 atoms other than hydrogen having a chain of from 2 to 8 atoms comprised of carbon, nitrogen, and chalcogen of atomic no. 8 to 16;

Z is hydrogen, hydroxyl, alkoxyl of from 1 to 6 carbon atoms, a group forming an activated ester capable of amide formation in an aqueous medium, or a poly(amino acid) which is antigenic or an enzyme;

m is 0 or 1, when Z is a poly(amino acid) and is otherwise 1; and n is 1 when Z is other than a poly(amino acid) and is otherwise 1 to the molecular weight of Z divided by 1000.

2. A compound according to claim 1, wherein R is a 1-oxopolymethylene of from 3 to 5 carbon atoms.

3. A compound according to claim 2, wherein R is of 4 carbon atoms.

4. A compound of the formula:

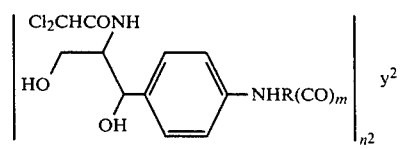

wherein:

R is a saturated aliphatic linking group of from 2 to 8 carbon atoms having from 0 to 1 oxo-carbonyl group at the terminus bonded to nitrogen;

$Y^2$ is hydrogen, hydroxyl, alkoxyl from 1 to 6 carbon atoms, or a group forming an activated ester capable of amide formation in an aqueous medium;

m is 1;

$n^2$ is 1.

5. A compound according to claim 4, wherein R is α-oxopentamethylene, $N^2$ is 1, and $y^2$ is OH.

* * * * *